(12) United States Patent
Ge et al.

(10) Patent No.: US 10,724,959 B2
(45) Date of Patent: Jul. 28, 2020

(54) SUBSTANCE DETECTION

(71) Applicant: Hewlett-Packard Development Company, L.P., Houston, TX (US)

(72) Inventors: Ning Ge, Palo Alto, CA (US); Steven Barcelo, Palo Alto, CA (US); Anita Rogacs, San Diego, CA (US); Helen A Holder, Palo Alto, CA (US)

(73) Assignee: Hewlett-Packard Development Company, L.P., Spring, TX (US)

( * ) Notice: Subject to any disclaimer, the term of this patent is extended or adjusted under 35 U.S.C. 154(b) by 48 days.

(21) Appl. No.: 15/764,322

(22) PCT Filed: Nov. 13, 2015

(86) PCT No.: PCT/US2015/060701
§ 371 (c)(1),
(2) Date: Mar. 28, 2018

(87) PCT Pub. No.: WO2017/082933
PCT Pub. Date: May 18, 2017

(65) Prior Publication Data
US 2018/0275066 A1    Sep. 27, 2018

(51) Int. Cl.
*G01J 3/44* (2006.01)
*G01N 21/65* (2006.01)
(Continued)

(52) U.S. Cl.
CPC ............. *G01N 21/658* (2013.01); *G01N 1/44* (2013.01); *G01N 21/648* (2013.01);
(Continued)

(58) Field of Classification Search
CPC ........ G01N 21/658; G01N 1/44; G01N 33/04; G01N 21/648; G01N 27/223; G01N 33/22;
(Continued)

(56) References Cited

U.S. PATENT DOCUMENTS 4,737,472 A    4/1988    Schaber et al.
6,485,913 B1    11/2002    Becker et al.
(Continued)

FOREIGN PATENT DOCUMENTS

CN    1808110    7/2006
CN    101155633    4/2008
(Continued)

OTHER PUBLICATIONS

Schmidt, Michael Stenbæk, et al. "Large area fabrication of leaning silicon nanopillars for surface enhanced Raman spectroscopy." Advanced Materials, 2012. OP11-OP18. vol. 24 No. 10.
(Continued)

*Primary Examiner* — Abdullahi Nur
(74) *Attorney, Agent, or Firm* — Dierker & Kavanaugh PC (57) ABSTRACT

In an example implementation, a substance detection method includes sensing for fluid in a chamber of a substance detection device. When fluid is sensed in the chamber, the method includes sensing again for fluid in the chamber. When no fluid is sensed in the chamber, the method includes initiating a substance detection process.

15 Claims, 6 Drawing Sheets

(51) Int. Cl.
*G01N 27/22* (2006.01)
*G01N 33/04* (2006.01)
*G01N 21/64* (2006.01)
*G01N 1/44* (2006.01)
*B01L 3/00* (2006.01)
*G01N 33/22* (2006.01)

(52) U.S. Cl.
CPC ........... *G01N 27/223* (2013.01); *G01N 33/04* (2013.01); *B01L 3/502715* (2013.01); *G01N 33/22* (2013.01)

(58) Field of Classification Search
CPC ........ G01N 33/28; G01N 33/00; G01N 33/48; G01N 21/00; B01L 3/502715
See application file for complete search history.

(56) References Cited

U.S. PATENT DOCUMENTS

| | | |
|---|---|---|
| 6,614,523 B1 | 9/2003 | Boss et al. |
| 8,792,095 B2 | 7/2014 | Piorek et al. |
| 8,994,937 B2 | 3/2015 | Mourey et al. |
| 2002/0118027 A1 | 8/2002 | Routkevitch et al. |
| 2007/0210068 A1* | 9/2007 | Reusche ............... A01K 1/0158 219/494 |
| 2012/0105841 A1 | 5/2012 | Hu et al. |
| 2013/0111986 A1 | 5/2013 | Leiser et al. |
| 2013/0219997 A1* | 8/2013 | Sullivan .................. E21B 49/10 73/53.01 |
| 2017/0269056 A1* | 9/2017 | Ciampini .............. C09D 163/04 |

FOREIGN PATENT DOCUMENTS

| | | |
|---|---|---|
| EP | 0319686 | 6/1989 |
| JP | 2001244311 | 9/2001 |
| JP | 2012-242272 A | 12/2012 |
| WO | WO-2011016888 | 2/2011 |
| WO | WO-2013162514 | 10/2013 |
| WO | WO-2014-142913 A1 | 9/2014 |

OTHER PUBLICATIONS

Haynes, et al. "Surface-enhanced Raman sensors: early history and the development of sensors for quantitative biowarfare agent and glucose detection." Journal of Raman Spectroscopy 36, No. 6-7 (2005): 471-484.

Luo, Yongming, "Synthesis and Characterization of Hydrothermal Stable Mesoporous Molecular Sieves and Functional Mesoporous Oxides," Zhijiang University Dissertation, 187 pages (Jun. 2006).

* cited by examiner

SUBSTANCE DETECTION

BACKGROUND

Surface Enhanced Raman Spectroscopy (SERS) may be used in various industries to detect the presence of an analyte. For example, SERS may be used in the security industry to detect and/or scan for explosives (e.g., detecting and/or scanning baggage at airports for explosives and/or other hazardous materials). Alternatively, SERS may be used in the food industry to detect toxins or contaminants in water and/or milk.

BRIEF DESCRIPTION OF THE DRAWINGS

Examples will now be described with reference to the accompanying drawings, in which.

Throughout the drawings, identical reference numbers designate similar, but not necessarily identical, elements.

DETAILED DESCRIPTION

There are various applications for devices that are capable of detecting or testing for the presence of a substance of interest. For example, substance detection/test devices are useful to detect the presence of explosives, toxins or hazardous substances at airports, manufacturing facilities, food processing facilities, drug preparation plants, and so on. The proper functioning of some substance detection devices can depend in part on protecting the substrates of the devices from contamination. A substrate can be contaminated if it is prematurely exposed to the environment or to a substance (e.g., an analyte) that the substrate is intended to detect. Premature exposure to the environment or to the substance of interest can cause the substrate to oxidize and be less effective in detecting the substance once the device substrate is intentionally exposed to the substance.

One way to reduce the chance of substrate contamination is to reduce the amount of time the device sits idle once it is ready to be tested for a substance of interest. In some examples, a fluid/liquid that potentially carries a substance of interest is introduced into a chamber of a substance detection device. After the fluid has evaporated from the chamber, the device can be tested for the presence of the substance. However, determining when the fluid has fully evaporated from the chamber can be challenging. For example, it is difficult to determine by observation with the naked eye whether or not the fluid has fully evaporated. If the device is tested for the substance of interest while there is still fluid present in the chamber, the test results can be inaccurate. However, waiting for an extended period of time to ensure that the fluid has fully evaporated from the chamber is costly in terms of time and money, and can also lead to inaccurate test results due to device contamination. The more time that passes between when the fluid has fully evaporated and the initiation of device testing to detect the substance of interest, the greater the chances are that the device substrate will be contaminated due to exposure to the open air. Thus, testing for a substance of interest at the moment the fluid has fully evaporated from the device chamber reduces the chances of contamination and improves the accuracy of the test results.

Accordingly, examples of substance detection discussed herein include an ability to sense and monitor the presence and/or level of fluid within a substance detection/test device. A closed-loop process of sensing fluid within the chamber of a substance detection device enables accurate control over when a substance detection process begins following the introduction of the fluid into the device chamber. Sensing for fluid within the chamber can be repeated in a continuous sensing loop as fluid is being sensed (i.e., a wet condition), and the sensing can cease once fluid is no longer being sensed. When fluid is no longer sensed within the chamber (i.e., a dry condition), a substance detection process can be initiated to identify a substance of interest that was carried into the chamber with the fluid.

The process of sensing fluid can also include sensing the level of the fluid remaining in the chamber of a substance detection device. Sensing the fluid level can provide an indication as to how fast the fluid is evaporating from the chamber. In some examples, the sensed fluid level can be used to determine whether to apply heat within the chamber (as well as how much heat to apply) in order to accelerate evaporation of the fluid. The amount of heat applied within the chamber can be tuned to the sensed fluid level.

In one example, a substance detection method includes, sensing for fluid in a chamber of a substance detection device. The fluid may contain a substance of interest (i.e., an analyte). When fluid is sensed in the chamber, the sensing for fluid can occur again. The sensing can continue until fluid is no longer sensed in the chamber. When no fluid is sensed in the chamber, a substance detection process is initiated.

In another example, a non-transitory machine-readable storage medium stores instructions that when executed by a processor of a reading device, cause the reading device to continually sense for fluid in a chamber of a substance detection device until no fluid is sensed in the chamber. When no fluid is sensed in the chamber, the reading device performs a substance detection process. As part of the substance detection process, the reading device can emit photons into the chamber, detect scattered photons, and identify a substance based on a characteristic of the scattered photons.

In another example, a substance detection system includes a fluid sensor to sense a fluidic condition in a chamber of a substance detection device. The system also includes a detection structure disposed within the chamber of the substance detection device. The system includes a reading device to receive a signal from the fluid sensor that indicates the fluidic condition. The reading device is to detect a substance of interest in the detection structure when the fluidic condition is a dry condition.

In general, example substance detection/test devices for the analysis of various substances can be used with surface Enhanced Raman spectroscopy, Enhanced Fluorescence spectroscopy, or Enhanced Luminescence spectroscopy, which can each be used to detect the presence of a substance of interest in or on a substance detection/test device. Example substance detection devices include metal or conductive orifice plates or housings that protect a substrate of a device from exposure to the environment and reduce (e.g. prevent) oxidation or other contamination of the substrate and associated surface structures prior to use. Example devices additionally include fluid slots for the introduction of fluid into the devices, sensors to sense the presence and/or level of fluid in the devices, and heaters to generate heat to speed the evaporation of fluid from the devices. The fluid slot can be used to controllably and precisely deliver a fluid solution or chemical to a testing chamber of a substance detection device. The sensor can be implemented by a sensing capacitor to measure impedance and/or capacitance of the fluid solution in order to identify the presence or absence of the fluid within the chamber and/or a level of the fluid within the chamber. In some examples, the measured impedance and/or capacitance can be used to identify a parameter or property of a fluid and/or substance in the chamber. A heater can be implemented by a low temperature resistance heater used to quickly dry and evaporate the fluid from the chamber in order to prepare the substance detection device for further analysis including a substance detection process.

In some examples, a controller manages various aspects of a substance detection process. In one aspect, the controller can implement a closed-loop fluid sensing process to determine the status of fluid within the chamber of a substance detection device. In one example, the controller can sense for fluid within the chamber to determine if previously introduced fluid has been fully evaporated from the chamber. Sensing for fluid can be continuous and/or can include sensing based on a time interval. The controller can continue sensing for fluid within the chamber until it determines that the fluid has fully evaporated. Thus, the controller can determine if the chamber is "wet" or "dry". Furthermore, the closed-loop sensing enables the controller to determine the precise moment when the chamber becomes "dry". This determination enables the controller to initiate and perform a substance detection process to detect if a substance of interest (i.e., an analyte) was present within the fluid.

In another example of a closed-loop fluid sensing process, the controller can sense the level of fluid within the chamber of a substance detection device. Determining the level of fluid within the chamber at a given moment can enable the controller to initiate a heating action to heat the fluid in the chamber in order to accelerate evaporation of the fluid from the chamber. Repeated sensing of the fluid level in the chamber enables the controller to modify the amount of heat applied to the fluid as the fluid level changes. In one example, when sensing indicates the fluid level is higher (e.g., above a given threshold), the controller can increase energy to a resistive heating element located within the chamber to add more heat, and when sensing indicates the fluid level is lower (e.g., below a given threshold), the controller can reduce or eliminate energy to the heating element to add less heat or no heat at all. The ability to control the amount of heat within the chamber based on sensed fluid levels enables the controller to accelerate evaporation of the fluid while avoiding high temperatures that may cause unwanted results, such as unwanted chemical reactions within the chamber. This manner of closed-loop fluid level sensing within the chamber enables the controller to determine the precise moment when fluid in the chamber has fully evaporated and the chamber is "dry". The controller can then initiate and perform a substance detection process to detect a substance of interest (i.e., an analyte) at an opportune time that helps to reduce the possibility of device contamination and increases overall efficiency in the substance detection process.

In some examples, a substance detection device includes an orifice plate, a sensor, a heater, and a substrate on which nanostructures and nanoparticles are positioned. In some examples, to couple or integrate the orifice plate with the wafer or substrate, a concave side of the orifice plate is positioned to face the substrate such that a chamber is defined between the orifice plate and the wafer or substrate. In some such examples, the sensor, the heater, and the nanostructures and nanoparticles are positioned within the chamber. Positioning the nanostructures and nanoparticles within the chamber helps prevent premature exposure to a substance that the nanostructures and nanoparticles are intended to detect. The orifice plate can be coupled to the wafer or substrate using a gang-bond process (e.g., thermoscompression bonding to bond metals). To reduce or even prevent the unintentional exposure of the nanostructures and nanoparticles to a substance such as an analyte that the nanostructures and nanoparticles are intended to detect, a polymer tape covers fluidic inlet ports or apertures of the orifice plate.

During use of an example substance detection device, the polymer tape can be at least partially removed from the orifice plate to open and expose a fluid slot/port, an aperture, the chamber, the substrate, and the nanostructures and nanoparticles to the environment. In one example, a fluid solution or chemical can be controllably delivered to the chamber through an aperture and/or fluid slot of the device. After the substrate, nanostructures and nanoparticles have been exposed to the fluid solution, a sensor can sense a fluidic condition in the chamber and a substance detection process can be initiated based on the fluidic condition. A substance of interest can be detected based on a characteristic of the substance determined from photon scattering off the nanostructures and nanoparticles. In some examples the sensor may measure a value of a parameter (e.g., impedance) of the substance which can be compared to a reference parameter. Additionally or alternatively, after the substrate, nanostructures, and nanoparticles have been exposed to the fluid solution, the heater may heat the substance to increase the rate at which the fluid dries on the nanostructures and nanoparticles to more quickly ready the substrate, nanostructures, and nanoparticles for further analysis.

As the fluid solution dries or evaporates from the chamber of the substance detection device, a substance carried within the fluid can dry on the nanostructures and nanoparticles in the chamber. The detection device can be placed in or adjacent to a reading device. An example reading device can include a light source that illuminates the substrate and the nanostructures and nanoparticles in the chamber. In some examples, the light scattered by the substrate, nanostructures and nanoparticles (e.g., Raman scattering in Surface Enhanced Raman spectroscopy, fluorescence in Enhanced Fluorescence spectroscopy, or luminescence in Enhanced Luminescence spectroscopy) is monitored using a spectrometer, photodetector, etc., having appropriate guiding and/or filtering components. In some examples, the results obtained by the reading device are displayed on a monitor and are indicative of detection or no detection of a substance of interest (i.e., a substance being tested for).

Figure 1:
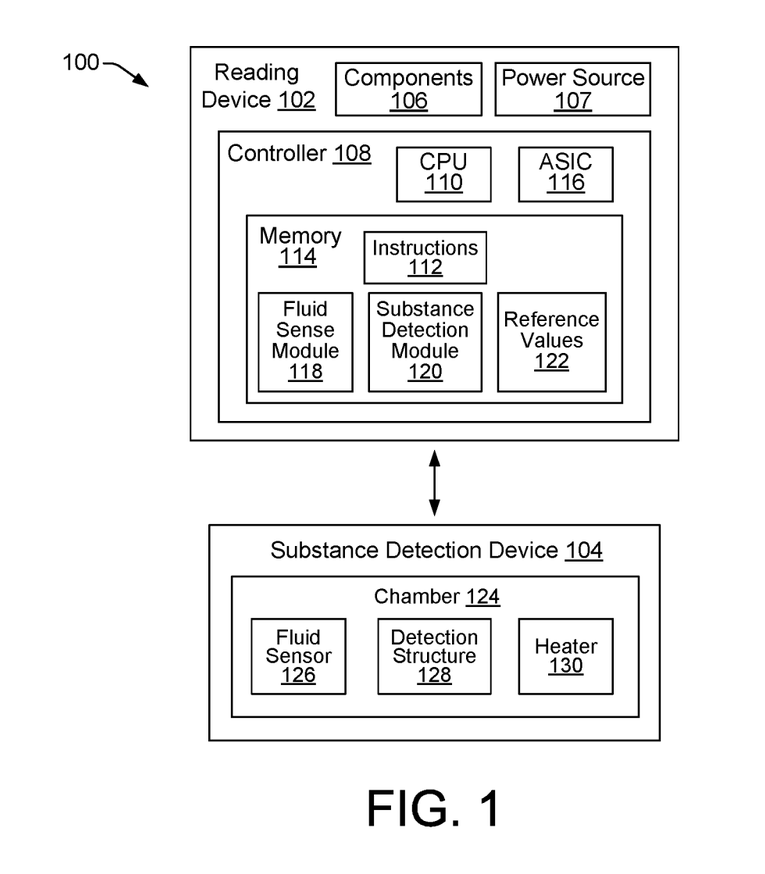
FIG. 1 shows an example of a substance detection system that includes a reading device and a substance detection device.

FIG. 1 shows an example of a substance detection system 100 that includes a reading device 102 and a substance detection device 104. The reading device 102 includes several substance reading components 106, a power source 107, and a controller 108. Substance reading components 106 can include, for example, a light source, a photodetector, and a display/monitor, which can facilitate an analysis of the substance detection device 104 during a substance detection process, as discussed in greater detail below with reference to FIGS. 7 and 8.

Controller 108 controls different aspects of the substance detection system 100, including a fluid sensing process and a substance detection process. Controller 108 includes a processor (CPU) 110, firmware and/or software such as executable instructions 112, memory components 114 including volatile and non-volatile memory components, and other electronics (not shown) for communicating with, analyzing, and controlling substance detection device 104. In some examples, controller 108 may include an application specific integrated circuit (ASIC) 116 to execute processes for communicating with, analyzing, and controlling substance detection device 104. The components of memory 114 comprise non-transitory, machine-readable (e.g., computer/processor-readable) media that provide for the storage of machine-readable coded program instructions, data structures, program instruction modules, and other data for the reading device 102, such as modules 118, 120, instructions 112, and reference values 122. The program instructions, data structures, and modules stored in memory 114 may be part of an installation package that can be executed by a processor (CPU) 110 to implement various examples, such as examples discussed herein. Thus, memory 114 may be a portable medium such as a CD, DVD, or flash drive, or a memory maintained by a server from which the installation package can be downloaded and installed. In another example, the program instructions, data structures, and modules stored in memory 114 may be part of an application or applications already installed, in which case memory 114 may include integrated memory such as a hard drive.

Figure 2:
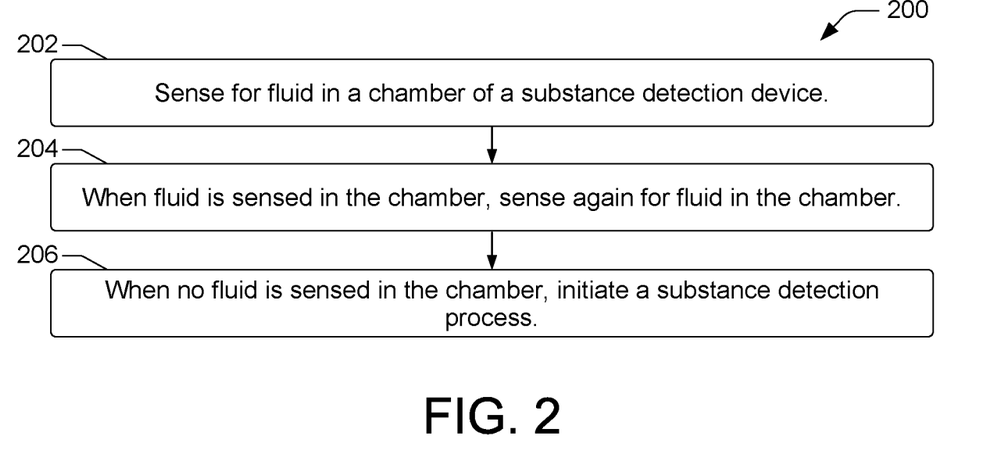
FIG. 2 shows a flow diagram that illustrates an example method of fluid sensing and substance detection.

The fluid sense module 118 comprises machine-readable instructions executable by the CPU 110 and/or ASIC 116 to perform fluid sensing of the substance detection device 104. FIG. 2 shows a flow diagram that illustrates an example method 200 of such fluid sensing and substance detection. Referring to FIGS. 1 and 2, during operation of the substance detection system 100, after fluid has been introduced into a chamber 124 of the substance detection device 104, the fluid sense module 118 senses for fluid (block 202, FIG. 2) through a fluid sensor 126 located within the chamber 124. While sensing for fluid, the fluid sense module 118 receives signals from the fluid sensor 126 that can indicate various fluidic conditions within the chamber 124. In an example, the fluid sensor 126 can indicate the presence or absence of fluid within the chamber 124. Thus, the fluid sensor 126 can provide signals indicating that no fluid is in the chamber 124 (i.e., a "dry" condition) which means that previously introduced fluid has fully evaporated from the chamber 124. Conversely, the fluid sensor 126 can provide signals indicating that there is fluid present within the chamber 124 (i.e., a "wet" condition) which means that previously introduced fluid has not fully evaporated from the chamber 124. When fluid is sensed in the chamber 124, the fluid sense module 118 and fluid sensor 126 can continue sensing for fluid (block 204, FIG. 2) in a closed-loop manner until the fluidic condition in the chamber 124 transitions from a "wet" condition to a "dry" condition. When no fluid is sensed in the chamber 124, or upon sensing the transition from a wet to a dry condition within the chamber 124, the CPU 110 and/or ASIC 116 of controller 108 can execute instructions from substance detection module 120 to initiate and perform a substance detection process (block 206, FIG. 2) that can detect a substance of interest on a detection structure 128 within the chamber 124. The substance detection process performed by module 120 is discussed below in greater detail with reference to FIGS. 7 and 8.

Figure 3:
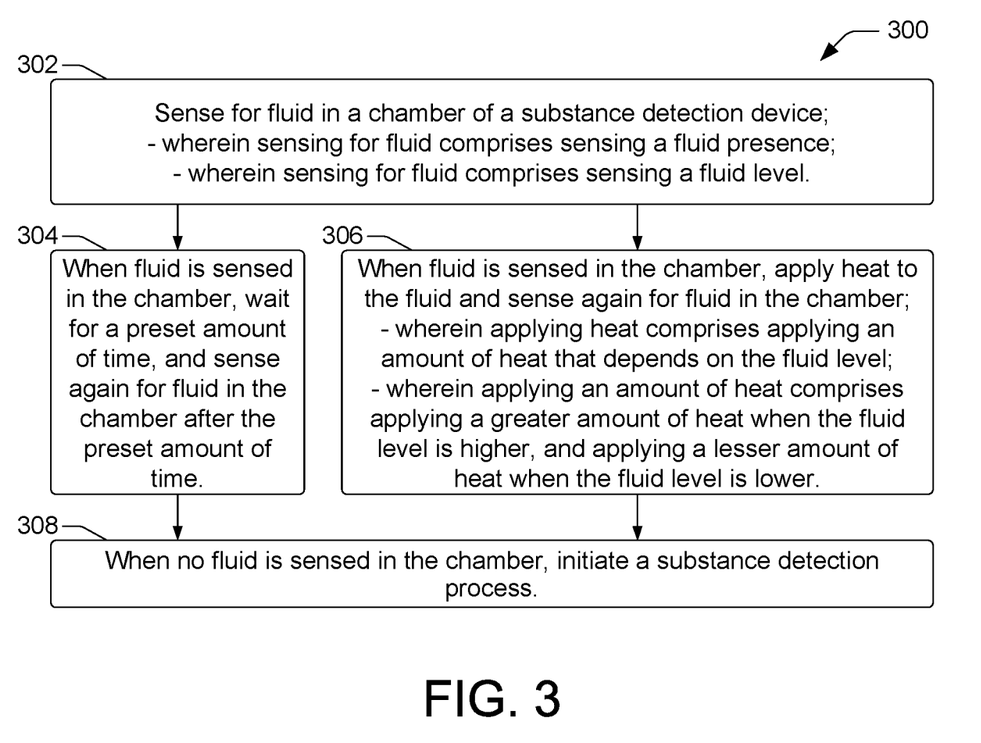
FIG. 3 shows a flow diagram that illustrates another example method of fluid sensing and substance detection.

FIG. 3 shows a flow diagram that illustrates another example method 300 of fluid sensing and substance detection as controllable, for example, by the CPU 110 and/or ASIC 116 executing instructions from fluid sense module 118. Referring to FIGS. 1 and 3, after fluid has been introduced into a chamber 124 of the substance detection device 104, the fluid sense module 118 senses for fluid (block 302, FIG. 3) through a fluid sensor 126 located within the chamber 124. While sensing for fluid, the fluid sense module 118 receives signals from the fluid sensor 126 that can indicate various fluidic conditions within the chamber 124. In an example, the fluid sensor 126 can indicate the presence or absence of fluid. In another example, the fluid sensor 126 can indicate a fluid level within the chamber 124.

When fluid is sensed in the chamber 124 (i.e., a "wet" condition within the chamber), in one example, the fluid sense module 118 can wait for a preset amount of time to pass by and then sense again for fluid in the chamber 124 (block 304, FIG. 3). The preset amount of time can be any amount of time that can facilitate the evaporation of fluid from the chamber. In addition, the preset amount of time can be an amount of time selected based on a fluid level sensed in the chamber. For example, when a higher fluid level is sensed in the chamber, the preset amount of time can be a greater amount of time, and when a lower fluid level is sense in the chamber, the preset amount of time can be a lesser amount of time. A higher fluid level within the chamber may comprise a fluid level that is greater than a percent of volume within the chamber, such as, for example, a fluid level that is greater than 50% of the volume of the chamber. A lower fluid level within the chamber may comprise a fluid level that is less than a percent of volume within the chamber, such as, for example, a fluid level that is less than 50% of the volume of the chamber. The percentages noted are provided by way of example, and are not intended to be limiting.

In another example, when fluid is sensed in the chamber 124 (i.e., a "wet" condition within the chamber), the fluid sense module 118 can apply heat to the fluid in the chamber and then sense again for fluid in the chamber (block 306, FIG. 3) to determine if all the fluid has evaporated from the chamber leading to a "dry" condition. Furthermore, the application of heat can include applying an amount of heat that depends on a fluid level that is sensed within the chamber 124. For example, applying heat based on a sensed fluid level can include applying a greater amount of heat when the fluid level in the chamber 124 is higher, and applying a lesser amount of heat when the fluid level is lower. As generally noted above, a higher fluid level within the chamber can be a fluid level that is greater than a percent of volume within the chamber, while a lower fluid level can be a fluid level that is less than a percent of volume within the chamber. Greater and lesser amounts of heat can be applied within the chamber 124 by controlling a power source 107 to supply varying amounts of current to a heater 130 within the chamber 124. A heater 130 may be implemented, for example, as a resistive heating element.

In an example, the repeated closed-loop process of sensing for fluid while controlling an amount of time between sensing and/or an amount of heat applied to the chamber 124 can continue until fluid is no longer sensed in the chamber 124 (i.e., until the chamber transitions from a "wet" condition to a "dry" condition). When fluid is no longer sensed in the chamber 124, the fluid sense module 118 can initiate a substance detection process (block 308, FIG. 3) through execution by the CPU 110 and/or ASIC 116 of machine-readable instructions from the substance detect module 120 stored in memory 114. A substance detection process as discussed below in more detail with reference to FIGS. 7 and 8, can detect a substance of interest on a detection structure 128 within the chamber 124.

Figure 4:
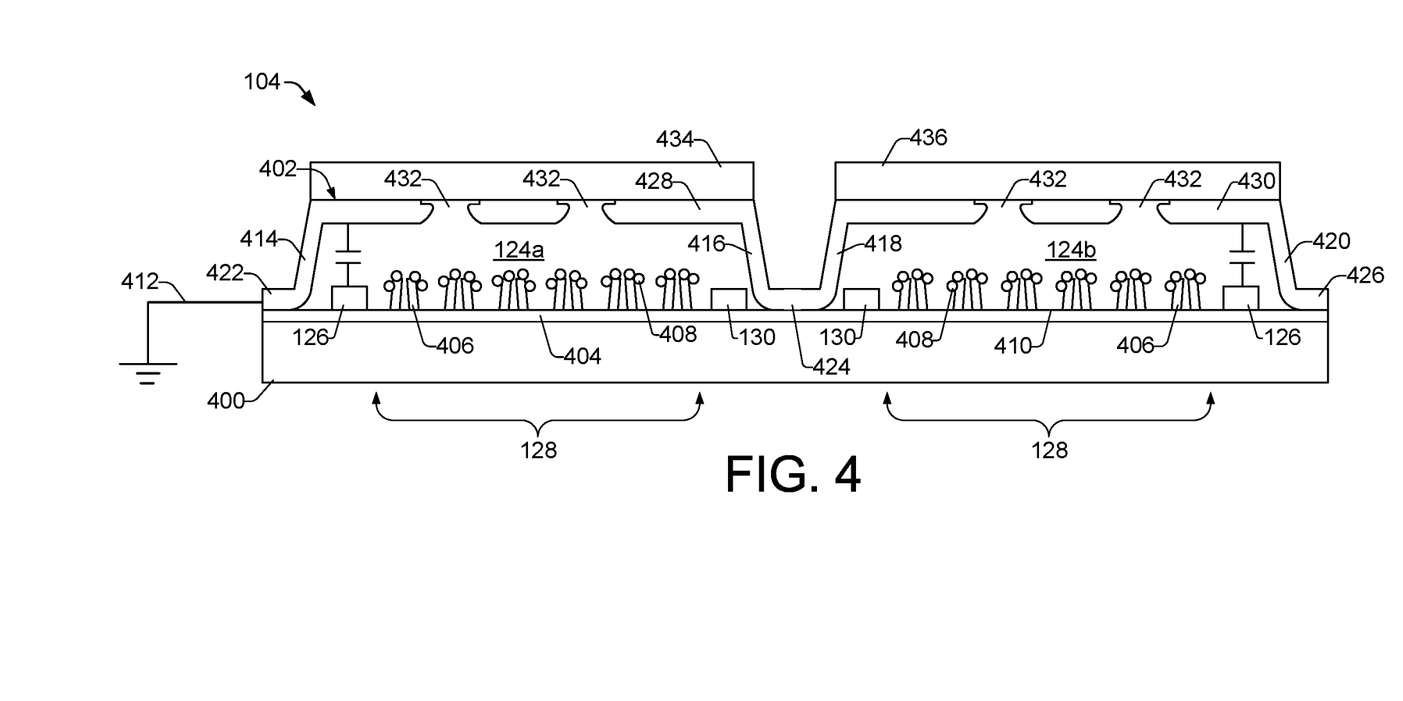
FIG. 4 shows a detailed example of a substance detection device.

FIG. 4 shows a more detailed example of a substance detection device 104. The example substance detection device 104 includes a substrate 400 coupled to a metallic and/or conductive orifice plate or housing 402 via a bond pad 404. The orifice plate 402 defines first and second chambers 124 (illustrated in FIG. 4 as chambers 124a and 124b) in which a fluid sensor 126, a heater 130, and nanostructures 406 and nanoparticles 408 are positioned. Together, nanostructures 406, nanoparticles 408, and substrate 400 generally comprise a detection structure 128 as mentioned above with reference to FIG. 1. The nanostructures 406 and nanoparticles 408 may be conical and pillar shaped. In some examples, after exposure to a fluid, substance or chemical, the pillar structures are pulled together to form nanoparticle assemblies having controllable geometries for enhanced spectroscopy analysis. In some examples, after exposure to a fluid, substance or chemical, the conical structures have relatively sharp tips that produce relatively strong enhancement for spectroscopy analysis. In some examples, the substrate 400 is transparent to enable detection and analysis of the nanostructures 406 and nanoparticles 408 through the substrate 400.

In the example substance detection device 104 shown in FIG. 4, the fluid sensor 126, heater 130, nanostructures 406 and nanoparticles 408 are positioned adjacent and/or coupled to a surface 410 of the substrate 400 and/or the bond pad 404. The substrate 400 may be made of any suitable material such as glass, plastic, paper, Polydimethylsiloxane, a transparent material, rubber and/or a membrane, for example. The orifice plate 402 may be made of any suitable material such as metal, nickel, gold and/or platinum, for example. The nanoparticles 408 may include gold and/or silver and/or any other element or chemical that may react with, respond to, collect, etc., a substance of interest such as an analyte.

The nanostructures 406 and nanoparticles 408 of the example substance detection device 104 facilitate detection of a substance of interest (i.e., an analyte) to which they have been exposed. In some examples, the analyte is contained in a fluid solution or chemical that has been introduced into a chamber 124 of the substance detection device 104. The example fluid sensor 126 is grounded 412, and is implemented by a sensing capacitor that measures impedance and/or capacitance of the fluid solution or chemical added to the chamber 124. As discussed above, the fluid sensor 126 can sense fluid within a chamber 124 to determine the presence (i.e., "wet" chamber condition) and absence (i.e., "dry" chamber condition) of fluid, as well as determining a fluid level within the chamber 124. In addition, in some examples, measured values from the sensor 126 may be used to determine a characteristic of the fluid solution or chemical. The heater 130 can be implemented, for example, by a low temperature resistance heater (e.g., a resistor) used to quickly dry the fluid solution in order to ready the substance detection device 104 for further analysis, including a substance detection process.

To define portions of the chambers 124a and 124b, the orifice plate 402 includes tapered portions 414, 416, 418, and 420; coupling portions 422, 424, and 426; and top portions 428 and 430. These portions of chambers 124a and 124b define apertures and/or fluidic inlet bores 432. In some examples, the coupling portions 422, 424, and 426, and the top portions 428 and 430, are spaced apart and substantially parallel to one another and are coupled via the respective tapered portions 414, 416, 418, and 420. As used herein, the phrase "substantially parallel" means within about a 10 degree skew of parallel. In other examples, the coupling portions 422, 424, and 426, are spaced apart from the top portions 428 and 430, but the coupling portions 422, 424, and 426, are not parallel to the top portions 428 and 430.

As shown in the example substance detection device 104 of FIG. 4, the first chamber 124a is defined by the tapered portions 414 and 416, and the top portion 428. The second chamber 124b is defined by the tapered portions 418 and 420, and the top portion 430. In this example, the coupling portion 424 is coupled to the substrate 400. The coupling portion 420 and the substrate 400 are joined to form a hermetic seal to separate the first and second chambers 124a and 124b, such that a first substance may be added to the first chamber 124a and a second substance may be added to the second chamber 124b without intermingling.

To enclose the first and second chambers 124a and 124b, seals 434 and 436 are removably coupled to the top portions 428 and 430. The seals 434 and 436 are hermetic seals that may be made of, for example, polymer tape, plastic, a transparent material, plastic sheeting, foil material, foil sheeting, a membrane, wax and/or Polydimethylsiloxane.

Figure 5:
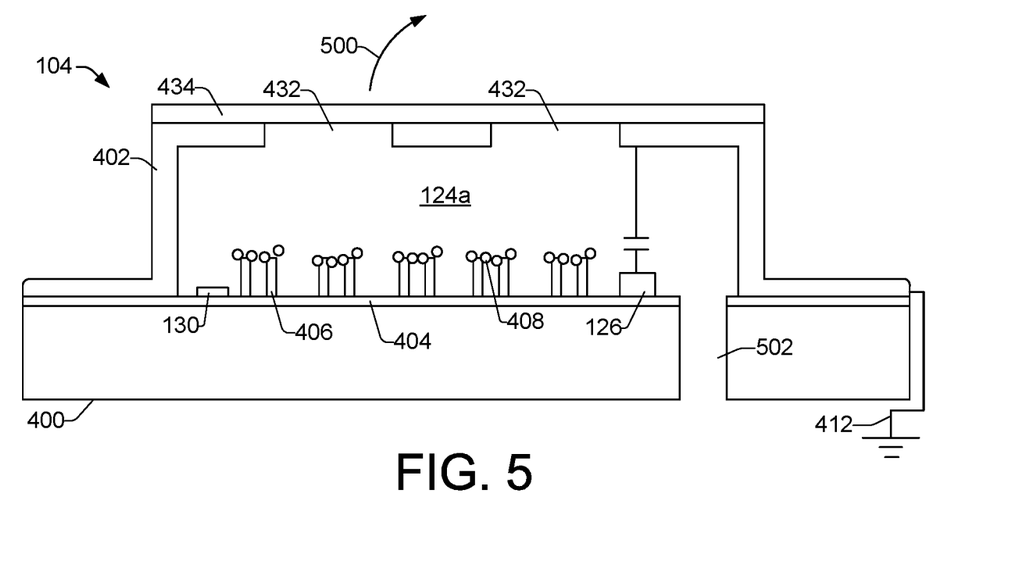
FIG. 5 shows an alternate view of a chamber of the example substance detection device of FIG. 4, with the seal about to be removed from the orifice plate.

FIG. 5 shows an alternate view of the first chamber 124a of the example substance detection device 104 of FIG. 4, with the seal 434 about to be removed in a direction generally indicated by arrow 500. In this view of chamber 124a, a slot 502 defined by the substrate 400 is shown. After the seal 434 is removed from the orifice plate or housing 402 of the substance detection device 104, air and/or other gas within a test environment (e.g., a room) in which the device 104 is positioned flows through the apertures 432 and into the chamber 124a where it is exposed to the nanostructures 406 and nanoparticles 408. The air and other gas within the test environment may or may not include the substance of interest (i.e., an analyte) that the nanostructures 406 and nanoparticles 408 are intended to detect.

Figure 6:
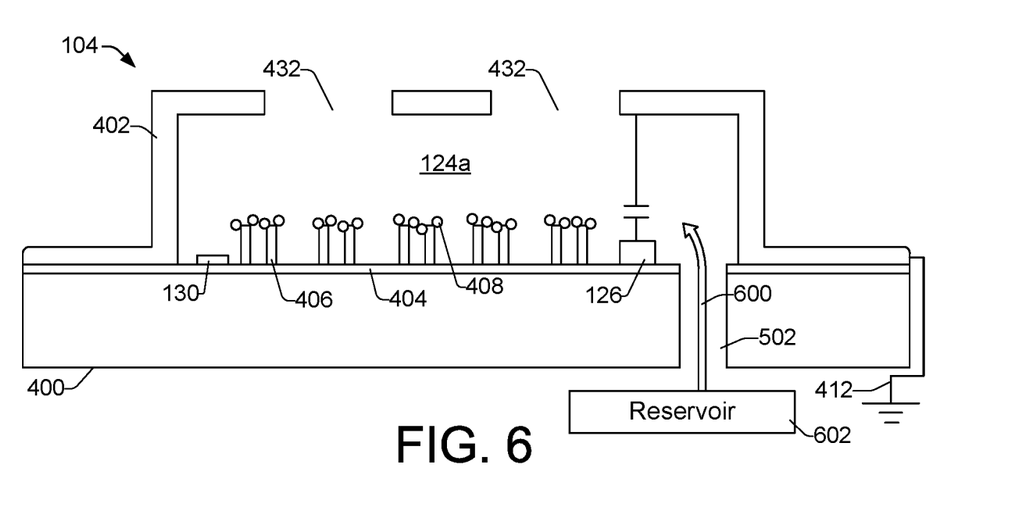
FIG. 6 shows an example substance detection device of FIG. 5 after the seal has been removed from the orifice plate.

FIG. 6 shows the example substance detection device 104 of FIG. 5 after the seal 434 has been removed from the orifice plate 402. In the example of FIG. 6, a fluid solution or chemical 600 to be analyzed is being added to the chamber 124a from a reservoir 602 through the slot 502 defined by the substrate 400. While FIG. 6 depicts the substance detection device 104 having the fluid solution 600 added to the chamber 124a with the seal 434 removed, in other examples, the seal 434 may remain attached to the orifice plate 402 while the fluid solution 600 is added to the chamber 124a. Depending on the detection circumstances, the fluid solution 600 may or may not include the substance of interest (i.e., the analyte) that the nanostructures 406 and nanoparticles 408 are intended to detect. In some examples, after the nanostructures 406 and nanoparticles 408 have been exposed to the fluid solution 600, the chamber 124a is re-covered by the seal 434 or another seal to ensure that the nanostructures 406 and nanoparticles 408 are not contaminated with exposure to a non-testing environment. In some examples, after the nanostructures 406 and nanoparticles 408 have been exposed to the fluid solution 600, the sensor 126 can measure a characteristic and/or value of the fluid solution 600. In some examples, the heater 130 heats the fluid solution 600 to accelerate evaporation which may leave particles of a substance that has been carried by the fluid solution 600 on the nanostructures 406 and nanoparticles 408. The particles may contain the substance of interest (i.e., the analyte) being tested for. In some examples, the evaporation of the fluid solution 600 pulls the nanostructures 408 and causes them to be positioned closer together.

Figure 7:
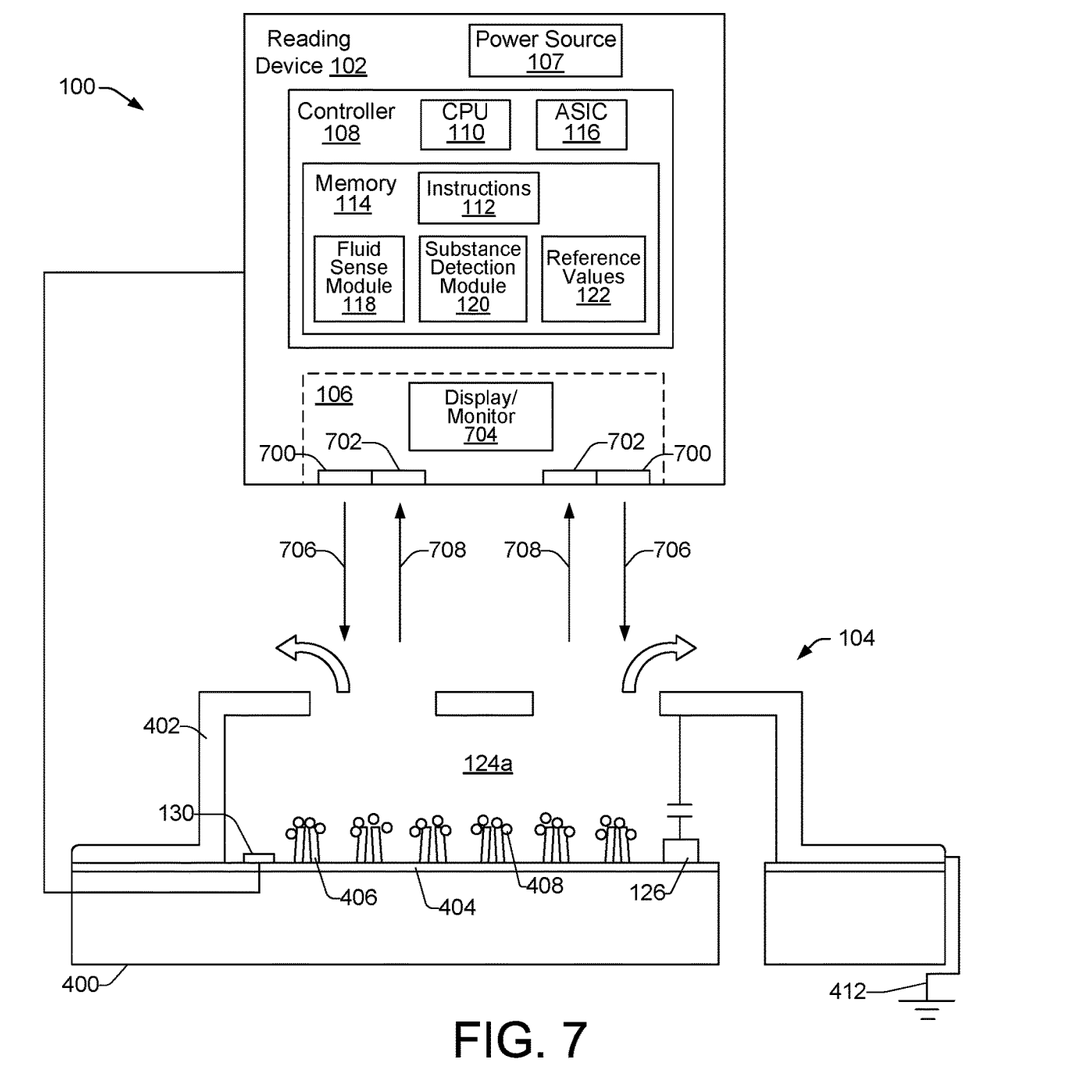
FIG. 7 shows another example substance detection system including a reading device and the substance detection device.

FIG. 7 shows an example substance detection system 100 as in FIG. 1, including a reading device 102 and the substance detection device 104 of FIG. 5. The substance detection device 104 is shown after exposure to an environment and/or an addition of a fluid solution 600 that may or may not contain a substance of interest (i.e., an analyte). In this example, the substance reading components 106 of the reading device 102 include a light source 700, a spectrometer and/or photodetector 702, and a display/monitor 704. The light source 700 emits photons 706 into the chamber 124a, and the photons 706 are scattered by the nanostructures 406 and nanoparticles 408. In some examples, some of the scattered photons 708 are detected and/or monitored by the spectrometer 702 of the reading device 102. Whether the substance of interest has been detected depends on one or more characteristics of the scattered photos 708 (e.g., a frequency shift, a wavelength change, etc.). In some examples, the reading device 102 uses the detected photons 708 along with appropriate guiding and filtering components to generate results which are displayed on a monitor 704. Displayed results can include, for example, information relating to the presence or absence of a substance of interest (i.e., an analyte to be detected). Additionally or alternatively, in some examples, the reading device 102 receives measured values from the sensor 126 and compares the measured values to reference values 122 to determine a characteristic of the substance of interest. The characteristic, that can be displayed on the monitor 704, may be the name of the substance of interest (i.e., an analyte) contained within the fluid solution 600 previously introduced into the chamber 124a.

Figure 8:
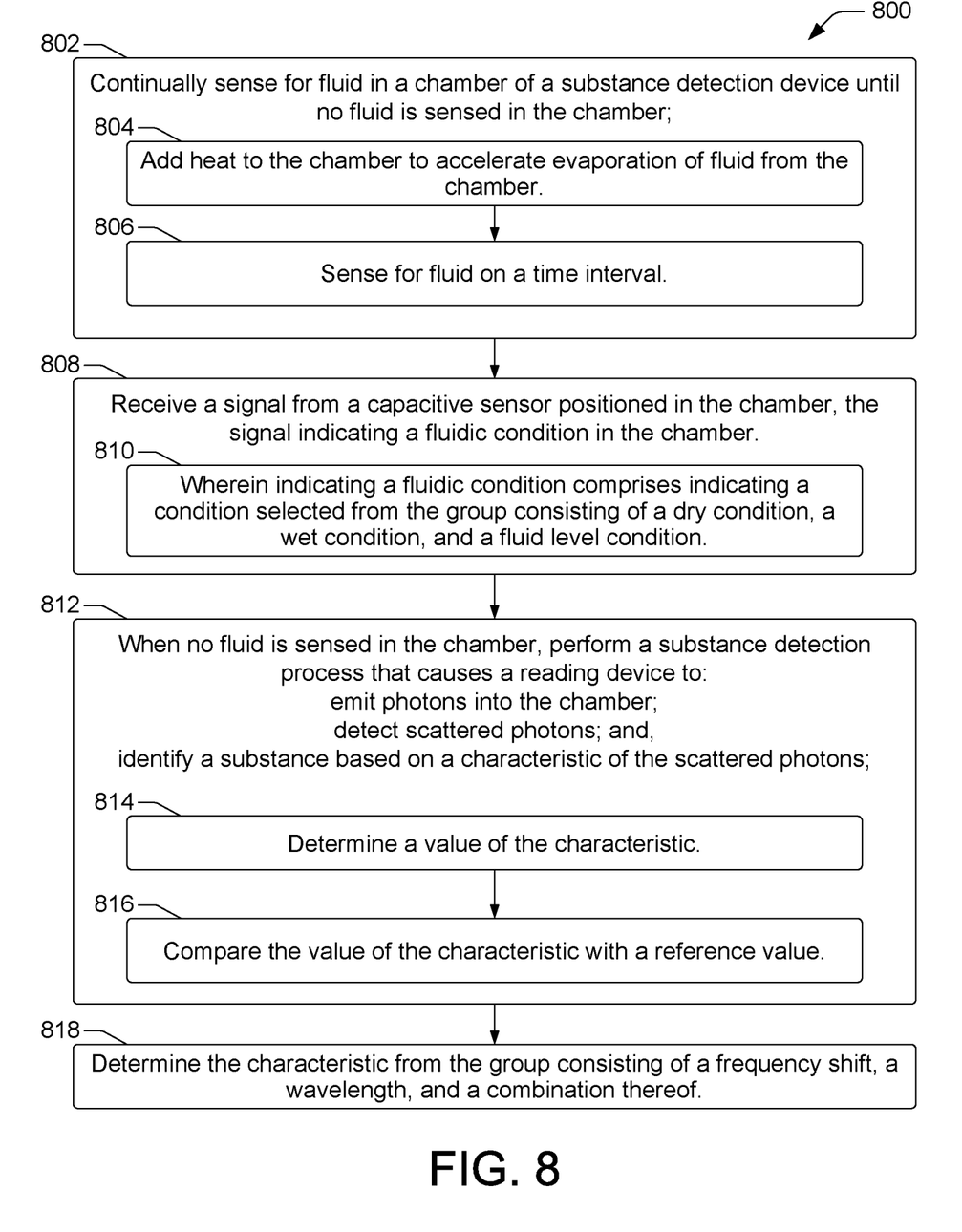
FIG. 8 shows a flow diagram that illustrates another example method of fluid sensing and substance detection.

FIG. 8 shows a flow diagram that illustrates another example method 800 of fluid sensing and substance detection as controllable, for example, by the CPU 110 and/or ASIC 116 of reading device 102 executing instructions from a fluid sense module 118 and substance detection module 120 stored in a memory 114. Referring now primarily to FIGS. 7 and 8, after fluid has been introduced into a chamber 124 of a substance detection device 104, the fluid sense module 118 continually senses for fluid in the chamber of the substance detection device until no fluid is sensed in the chamber (block 802, FIG. 8). In some examples, continually sensing for fluid can include adding heat to the chamber to accelerate evaporation of fluid from the chamber (block 804, FIG. 8) and sensing for fluid on a time interval (block 806, FIG. 8). Sensing for fluid on a time interval can include, for example, waiting an amount of time between each sense for fluid. In some examples, heat can be added to the chamber in addition to sensing for fluid on a time interval.

In some examples, fluid sensing in method 800 can include receiving a signal from a capacitive sensor positioned in the chamber (block 808, FIG. 8). The signal from the capacitive sensor can indicate a fluidic condition in the chamber. In some examples, indicating a fluidic condition with a signal from the capacitive sensor comprises indicating a dry condition in the chamber, a wet condition in the chamber, or a fluid level condition in the chamber (block 810, FIG. 8).

When no fluid is sensed in the chamber, the method 800 can continue with performing a substance detection process (block 812, FIG. 8). The substance detection process can cause a reading device to emit photons into the chamber, detect scattered photons, and identify a substance based on a characteristic of the scattered photons. Identifying a substance based on a characteristic can include determining a value of the characteristic (block 814, FIG. 8) and comparing the value of the characteristic with a reference value (block 816, FIG. 8). In some examples, determining a characteristic comprises determining the characteristic from a frequency shift, a wavelength, or a combination thereof (block 818, FIG. 8).

What is claimed is:

1. A substance detection method comprising:
    sensing for fluid in a chamber of a substance detection device;
    in response to sensing fluid in the chamber, sensing again for fluid in the chamber;
    in response to sensing no fluid in the chamber, initiating a substance detection process.

2. A method as in claim 1, further comprising:
    in response to sensing fluid in the chamber, waiting for a preset amount of time and sensing again for fluid in the chamber after the preset amount of time has passed.

3. A method as in claim 1, further comprising:
    in response to sensing fluid in the chamber, applying heat to the fluid and sensing again for fluid in the chamber.

4. A method as in claim 1, wherein sensing for fluid in a chamber comprises sensing a fluid level in the chamber.

5. A method as in claim 4, further comprising:
    applying an amount of heat to the fluid in the chamber, where the amount of heat depends on the fluid level; and
    sensing again for fluid in the chamber.

6. A method as in claim 5, wherein applying an amount of heat comprises applying a greater amount of heat when the fluid level is higher, and applying a lesser amount of heat when the fluid level is lower.

7. A non-transitory machine-readable storage medium storing instructions that when executed by a processor of a reading device, cause the reading device to:
    continually sense for fluid in a chamber of a substance detection device until no fluid is sensed in the chamber;
    in response to sensing no fluid in the chamber, perform a substance detection process that causes the reading device to:
    emit photons into the chamber;
    detect scattered photons; and,
    identify a substance based on a characteristic of the scattered photons.

8. A medium as in claim 7, wherein identifying a substance comprises:
    determining a value of the characteristic; and,
    comparing the value of the characteristic with a reference value.

9. A medium as in claim 7, the instructions further causing the reading device to determine the characteristic from the group consisting of a frequency shift, a wavelength, and a combination thereof.

10. A medium as in claim 7, the instructions further causing the reading device to receive a signal from a capacitive sensor positioned in the chamber, the signal indicating a fluidic condition in the chamber.

11. A medium as in claim 10, wherein indicating a fluidic condition in the chamber comprises indicating a condition selected from the group consisting of a dry condition, a wet condition, and a fluid level condition.

12. A medium as in claim 7, wherein continually sensing for fluid comprises:
adding heat to the chamber to accelerate evaporation of fluid from the chamber; and
sensing for fluid on a time interval.

13. A substance detection system comprising:
a fluid sensor to sense a fluidic condition in a chamber of a substance detection device;
a detection structure disposed within the chamber; and
a reading device to receive a signal from the fluid sensor indicating the fluidic condition, and to detect a substance of interest in the detection structure when the fluidic condition is a dry condition.

14. A system as in claim 13, further comprising:
a heater disposed within the chamber of the substance detection device; and
a power source, a processor, and a computer-readable medium containing instructions in the reading device, wherein the processor is to execute the instructions to:
monitor the fluidic condition; and
control power from the power source to the heater based on the fluidic condition to accelerate evaporation of fluid within the chamber to achieve the dry condition.

15. A system as in claim 14, wherein the reading device comprises a light source, a photodetector, and a monitor, and wherein the processor is to execute the instructions to detect the substance of interest by:
emitting photons from the light source into the chamber;
detecting photons scattered by the detection structure in the chamber; and
based on the scattered photons, displaying a result on the monitor regarding the substance of interest.

* * * * *